(12) United States Patent
Johnstone

(10) Patent No.: US 8,365,732 B2
(45) Date of Patent: Feb. 5, 2013

(54) WEARABLE PROTECTIVE DEVICE

(75) Inventor: Clive Johnstone, Abingdon (GB)

(73) Assignee: JSP Ltd., Oxfordshire (GB)

(*) Notice: Subject to any disclaimer, the term of this patent is extended or adjusted under 35 U.S.C. 154(b) by 549 days.

(21) Appl. No.: 12/610,662

(22) Filed: Nov. 2, 2009

(65) Prior Publication Data
US 2010/0126504 A1  May 27, 2010

Related U.S. Application Data

(60) Provisional application No. 61/182,172, filed on May 29, 2009.

(51) Int. Cl.
*A61M 11/00* (2006.01)

(52) U.S. Cl. ......... 128/206.17; 128/206.23; 128/206.21; 128/206.19

(58) Field of Classification Search .......... 128/206.12–206.27, 207.11
See application file for complete search history.

(56) References Cited

U.S. PATENT DOCUMENTS

| | | | |
|---|---|---|---|
| 4,098,270 A | 7/1978 | Dolby | |
| 4,296,746 A * | 10/1981 | Mason et al. | 128/201.15 |
| 4,784,131 A | 11/1988 | Schroeder | |
| 4,796,621 A * | 1/1989 | Barle et al. | 128/206.23 |
| 5,584,078 A * | 12/1996 | Saboory | 2/427 |
| 5,682,879 A * | 11/1997 | Bowers | 128/206.19 |
| 5,694,925 A * | 12/1997 | Reese et al. | 128/206.19 |
| 6,026,511 A * | 2/2000 | Baumann et al. | 2/9 |
| 6,176,239 B1 * | 1/2001 | Grove et al. | 128/206.24 |
| 6,543,450 B1 | 4/2003 | Flynn | |
| 2004/0237962 A1 | 12/2004 | Russell | |

FOREIGN PATENT DOCUMENTS

| | | |
|---|---|---|
| GB | 2414413 A | 5/2005 |
| RU | 2060739 C1 | 1/1992 |
| WO | WO9009209 | 8/1990 |
| WO | WO2008/038999 A1 | 4/2008 |

* cited by examiner

*Primary Examiner* — Steven Douglas
(74) *Attorney, Agent, or Firm* — Taft Stettinius & Hollister LLP; Keith Swedo

(57) ABSTRACT

A wearable protective device (100) including an eye shield (102), a holder (106) for a removable breathing filter (400), and an arrangement (104, 118) for fixing the device, in use, to a wearer's head. The eye shield and the holder are integrated or permanently connected together.

14 Claims, 5 Drawing Sheets

WEARABLE PROTECTIVE DEVICE

The present application claims priority from U.S. provisional patent application Ser. No. 61/182,172 filed on May 29, 2009 and British patent application no. 0821406.6 filed on 22 Nov. 2008.

FIELD OF THE INVENTION

The present invention relates to wearable protective devices.

BACKGROUND TO THE INVENTION

Many different types of facial masks for protecting the wearer against breathing in dangerous fumes, preventing cross-infection and the like are known. It is also known to wear goggles to protect eyes. Conventionally, breathing masks and goggles are separate items and have to be put on and taken off separately. This can be inconvenient for the wearer whilst working. Further, conventional spectacle-type arms for fitting goggles onto the head can be prone to slipping off unintentionally. This can be particularly problematic when the facemask interferes with the normal fit of the goggles/spectacles. Different facial shapes and different shapes of glasses/goggles can also mean that conventional facemasks can be uncomfortable to wear, or difficult to fit.

There is therefore a need for a wearable protective device that can be securely attached to a wearer's head during use and/or can provide a good degree of adjustability so that different shapes/sizes of faces can be easily and comfortably accommodated.

SUMMARY OF THE INVENTION

According to a first aspect of the present invention there is provided a wearable protective device including:
an eye shield;
a holder for a removable breathing filter, and
an arrangement for fixing the device, in use, to a wearer's head,
wherein the eye shield and the holder are integrated or permanently connected together.

The eye shield and the holder may be integrated or permanently connected together so that they cannot be separated in a non-destructive manner.

The eye shield may include goggle lenses or the like. The lenses can be designed to provide eye protection only and not to correct eyesight defects. The eye shield may formed of, or coated with, anti-mist material and/or anti-glare material and/or anti-smoke material and/or UV-protection material.

The holder may be pivotable with respect to the eye shield. The holder may be semi rigid and may be configured to receive/fit around at least part of an outer edge of the removable breathing filter.

The holder may include a bridge portion configured, in use, to fit on a nose bridge of the wearer. The eye shield (e.g. a lower portion of the eye shield) may be connected to the bridge portion of the holder, e.g. by means of at least one fixing device that extends through at least one corresponding aperture in the holder and the eye shield. The fixing device may include a moulded plastic pin. In an alternative embodiment a first portion of a flexible member is fixed to the eye shield and a second portion of the flexible member is fixed to the holder. The first portion of the flexible member may be fixed to a substantially central portion of the eye shield and the second portion of the flexible member may be fixed to a substantially central portion of the bridge portion of the holder. The bridge portion may include at least one slot or aperture adapted to assist with avoiding condensation developing within the holder.

The holder may include a chin portion configured, in use, to fit under/around a chin of the wearer.

The fixing arrangement may include a pair of arms, which may be pivotably connected to the eye shield. The arms may, in use, be generally aligned with an eye region of the wearer.

Alternatively or additionally, the fixing arrangement may include at least one elastic strap, which may be connected to at least one corresponding side portion/edge of the holder. In some embodiments, there can be two elastic straps, each of the elastic straps including an interengageable clasp or clip at its free end. The at least one elastic strap may, in use, be generally aligned with a mouth region of the wearer.

The removable breathing filter may be configured to be worn over a nose and mouth of the wearer. The removable breathing filter may be disposable, e.g. it may comprise a filtering face piece (FFP).

According to a further aspect of the present invention there is provided a wearable protective device including:
an eye shield;
a holder for a removable breathing filter, and
an arrangement for fixing the device, in use, to a wearer's head,
wherein the holder is pivotable with respect to the eye shield.

According to another aspect of the present invention there is provided a kit including a device substantially as described herein and at least one removable breathing filter.

Whilst the invention has been described above, it extends to any inventive combination of features set out above or in the following description. Although illustrative embodiments of the invention are described in detail herein with reference to the accompanying drawings, it is to be understood that the invention is not limited to these precise embodiments. As such, many modifications and variations will be apparent to practitioners skilled in the art. Furthermore, it is contemplated that a particular feature described either individually or as part of an embodiment can be combined with other individually described features, or parts of other embodiments, even if the other features and embodiments make no mention of the particular feature. Thus, the invention extends to such specific combinations not already described.

BRIEF DESCRIPTION OF THE DRAWINGS

The invention may be performed in various ways, and, by way of example only, embodiments thereof will now be described, reference being made to the accompanying drawings in which.

DETAILED DESCRIPTION OF THE DRAWINGS

Figure 1:
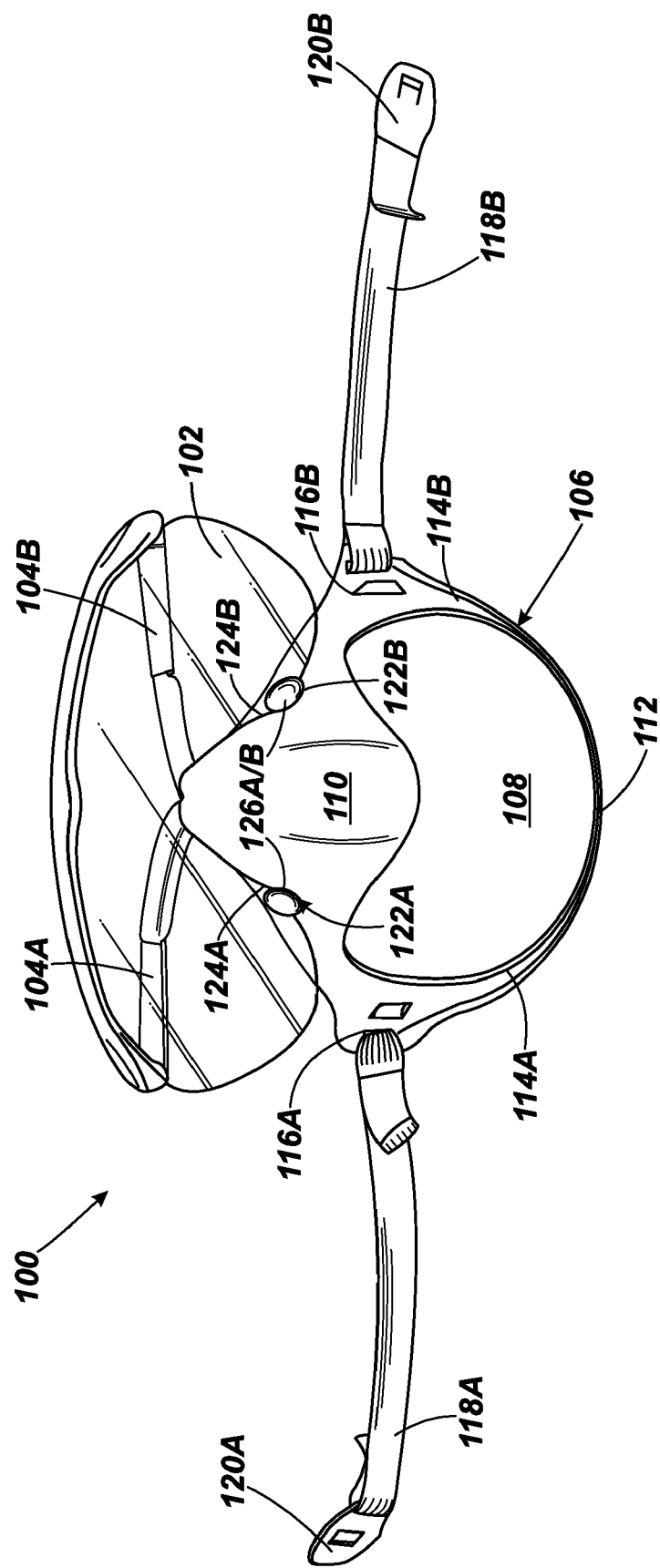
FIGS. 1, 2 and 3 are front, back and side, respectively, views of a first embodiment of the device.
Figure 2:
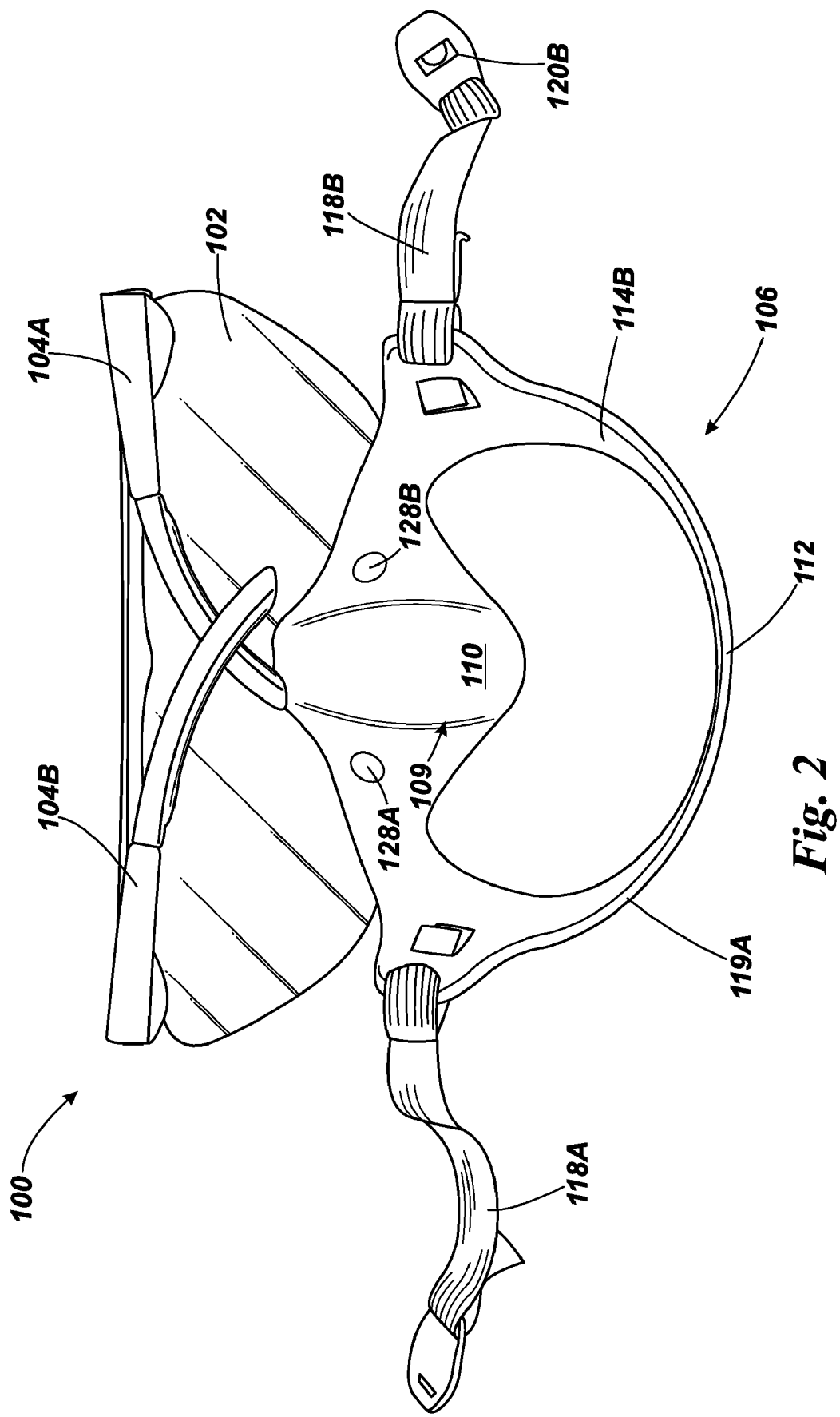
Figure 3:
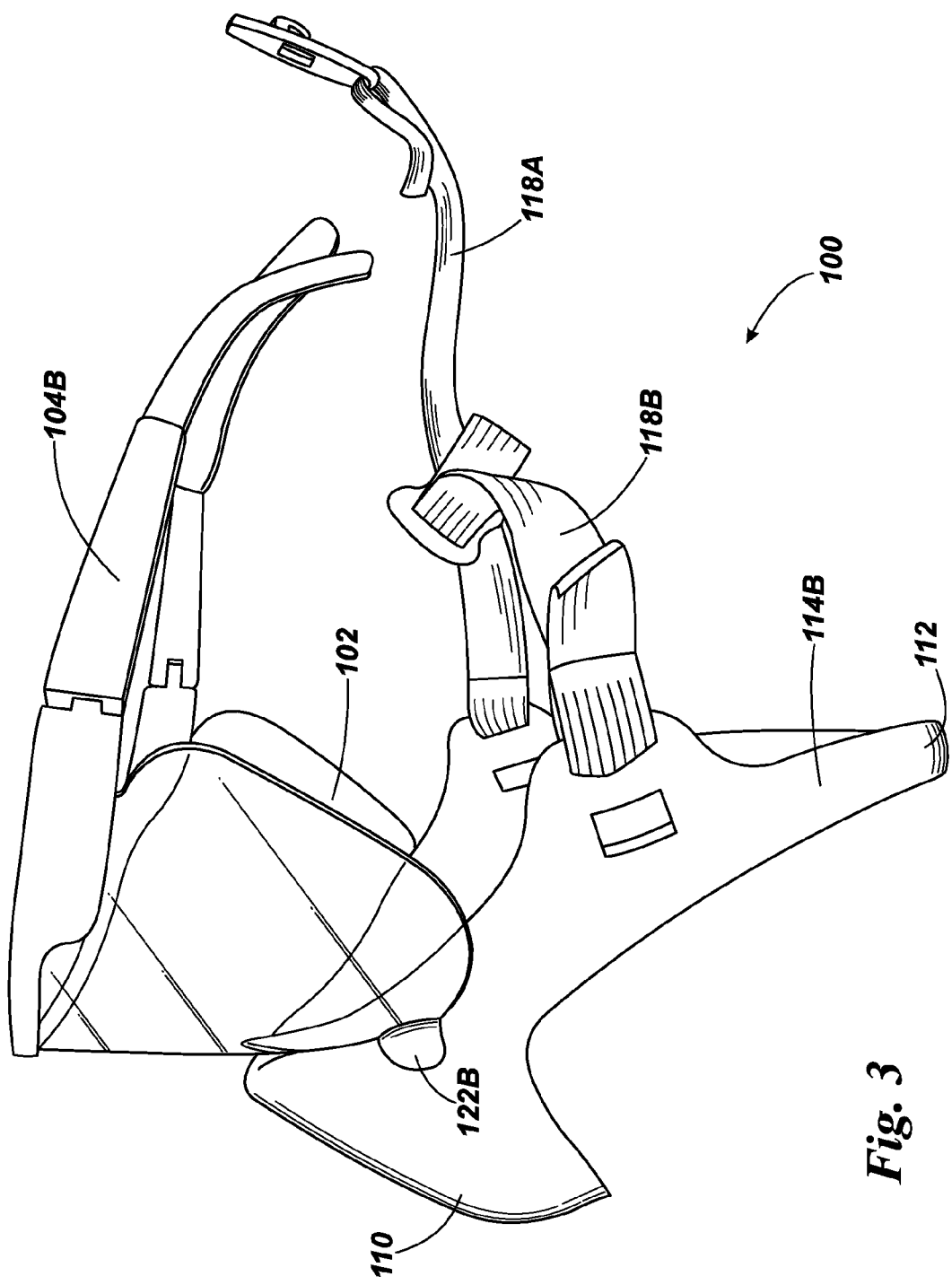

Referring to FIGS. 1 to 3, a first example of a protective device 100 is shown. The device includes an eye shield including a transparent plastic lens 102 having an upper rim to which a pair of arms 104A, 104B are pivotably connected (the arms are shown in a folded configuration in FIGS. 1 and 2 and in an extended configuration for fitting over the wearer's ears in FIG. 3). It will be understood that the eye shield shown in the Figures is exemplary only and variations are possible. For instance, the shield can be formed of more than one separate lens and an arrangement other than the spectacle-type arm may be provided for fitting the device onto the wearer's head.

The lens 102 can be formed of a flexible plastic material, such as polycarbonate, polyacetate or acrylic and the arms 104A, 104B and rim/frame of the eye shield may be formed of a semi-flexible plastic material, such as nylon or polypropylene, but it will be understood that other material, e.g. glass and metal, could be used. Further, the lenses may be at least partially formed of, or coated with, known materials having anti-mist and/or anti-glare and/or anti-smoke and/or anti-UV properties.

The device 100 further comprises a holder 106 for a removable breathing filter. The holder is formed so as to fit on/around the nose and mouth area of the wearer and includes an aperture 108 which, in use, can receive a major portion of the filter and allow the wearer to breath through that. The holder includes a bridge portion 110 that is configured to fit over the majority of the wearer's nose, but not the lower portion of the nose. The holder further also includes a chin portion 112 that is designed to extend around/under the wearer's chin in use. Side portions 114A, 114B connect the bridge portion to the chin portion and together all these portions define the outline of the aperture 108. The holder is formed of a flexible plastic, such as polyethylene, polypropylene, flexible PVC or a thermoplastic or thermosetting rubber. The inner surface of the holder can have small protrusions 109 arranged over it.

Each of the side portions includes an outer protruding area 116A, 116B that has a slot into which a respective elastic strap 118A, 118B is looped. The free end of each strap includes a clasp/clip 120A, 120B. In use, the straps are connected together around the back of the wearer's head. It will be understood that an alternative arrangement for attaching the holder to the wearer can be provided, e.g. a different type/arrangement of strap(s), or the holder could be shaped to fit further around the back of the wearer's head and hold it in place.

The eye shield 102 is permanently connected to the holder 106. By this it is meant that the two components are fixed to each other in a manner that is not intended to allow them to become separated during normal use, or without destroying/damaging at least part of the device 100, except with the use of special instructions or tools, e.g. when parts of the device need to be separated for the purpose of decontamination or sterilisation. In the example device 100, the permanent connection is provided by a two plastic fixing devices 122A, 122B that are located through respective apertures in the lens 102 and the bridge portion 110 of the holder. A first one of the fixing devices 122A (the left-hand one in FIG. 1) is fitted through an aperture (not visible) in a curved section 124A that extends out of a lower left-hand portion of the lens 102. There is a corresponding aperture (not visible) in a left-hand side area of the bridge portion 110. The second fixing device 112B fits through corresponding apertures in a right-hand curved extension 124B of the lens 102 and a right-hand area of the bridge portion 110 (the lens and holder are substantially symmetrical about a notional central line).

Each fixing device 122A, 122B may comprise a plastic member having a fixed disc-shaped head 126A, 126B (in FIG. 1) and a short shaft (not visible). During assembly, the shaft is inserted through the corresponding apertures in the lens and holder and then a second disc-shaped head 128A, 128B (in FIG. 2) is fixed to the free end of the shaft, thereby securing the lens and the holder between the two heads. The second head can include an aperture through which an enlarged tip of the shaft can be forced, but not easily removed. It will be appreciated that many different ways of permanently connecting the eye shield and the holder together are feasible, e.g. strong adhesives, heating/melting. Alternatively, the device 100 can be formed so that the eye shield and holder are integrated, e.g. moulded from one piece of flexible plastic.

Figure 4:
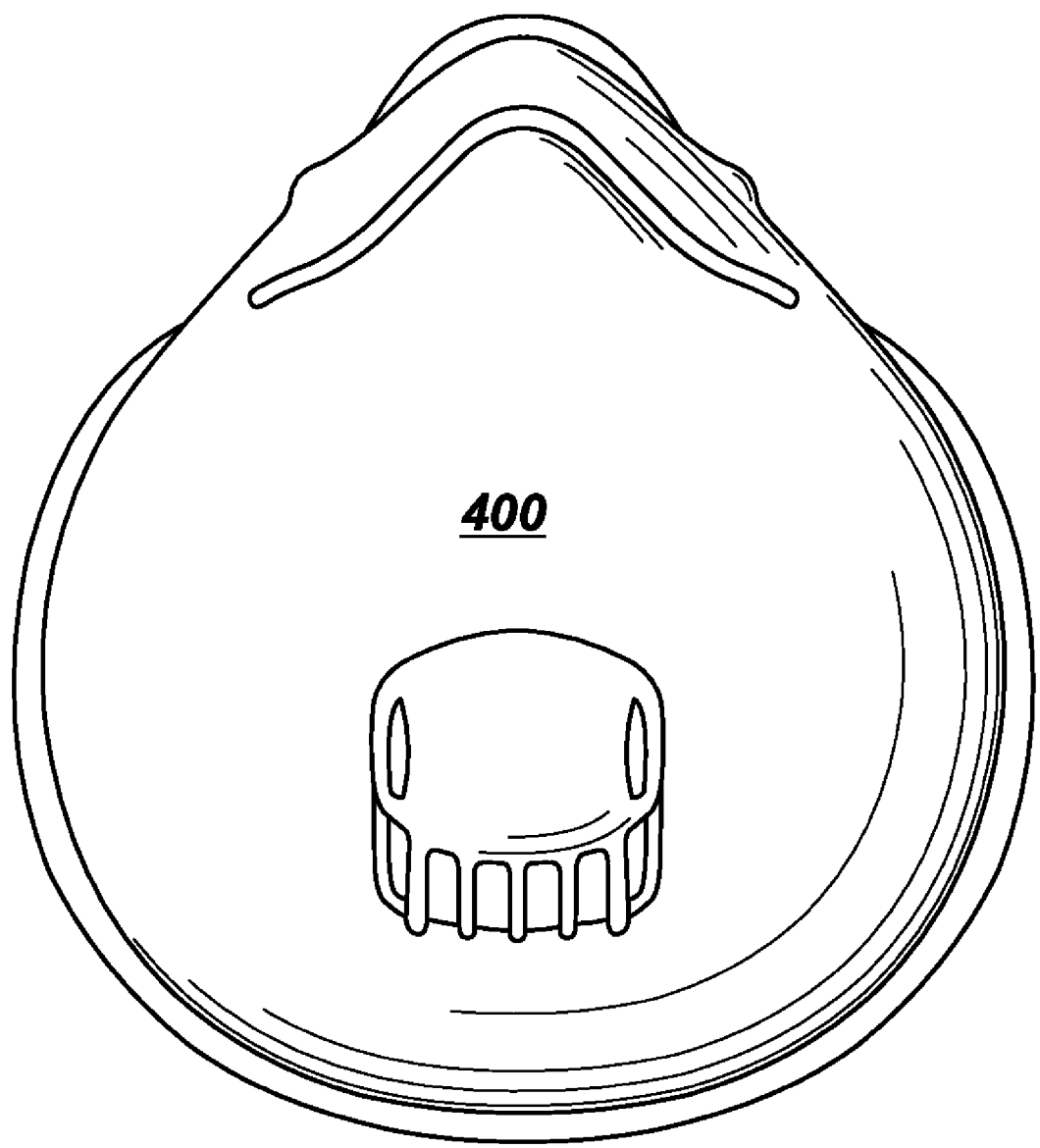
FIG. 4 is a front view of a filter that can be used in connection with the device.

FIG. 4 shows an example of a filter 400 that can be inserted into the holder 106. The example filter comprises a disposable filter face piece (FFP), such as ones produced by JSP Ltd of Oxford, United Kingdom. However, it will be understood that other filters could be used and the design of the holder 106/device 100 could be modified to accommodate filters having different dimensions/shapes.

In use, the user fits the filter 400 into the inner surface (shown in FIG. 2) of the holder 106. The user can then unfold the arms 104 of the eye shield and fit them on his head, as with a conventional pair of goggles. The user then presses the holder 106, fitted with the filter, over his nose/mouth area, such that the chin portion 112 fits under his chin. The flexible connection between the eye shield and the holder means that the holder can be pivoted with respect to the eye shield (and vice versa), allowing a comfortable fit for a wide range of face shapes/sizes. The user then draws the two elastic straps 118A, 1188 around the back of his head and engages their clips 120A, 120B. In some cases, this fitting operation will stretch and distort the holder 106, in particular the side portions 114A, 114B and this flexibility again assists with providing a comfortable fit. Having a single device comprising integrated/permanently connected eye shield and filter holder that is fixed to the wearer's head using two separate fixing arrangements (e.g. the spectacle-type arms and the elastic straps) means that it is less likely to be accidentally removed that separate goggles and masks (although it will be understood that versions of the device having just one of the fixing arrangements 104, 118 can be provided). Further, the device 100 can be re-used many times, with just the disposable filter 400 being replaced, which can result in economic advantages.

Figure 5:
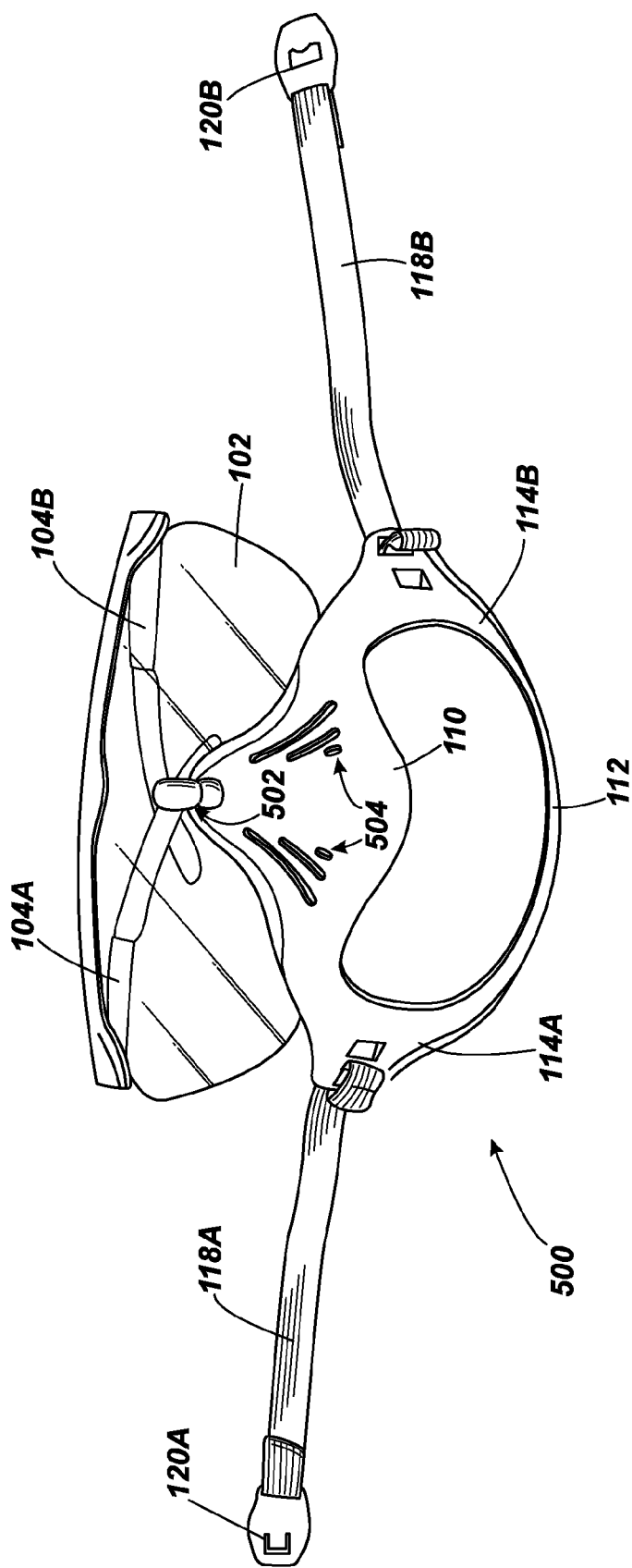
FIG. 5 is a front view of an alternative embodiment of the device.

FIG. 5 shows a front view of an alternative version of the protection device. The device 500 includes similar components/portions to the example 100 (and corresponding parts are given the same reference numerals as in FIGS. 1-3), but the eye shield 102 is not connected to the holder 106; instead an elongate member 502 formed of flexible plastic permanently connects the two items together. One end of the member 502 is fixed to a central portion of the eye shield 102, e.g. by means of a plastic fixing device fitting through an aperture. The other end of the member 502 is fixed to a central upper area of the bridge portion 110 of the holder 106, e.g. by means of a similar plastic fixing device/aperture arrangement. Again, this flexible connection allows the eye shield and the holder to pivot relative to each other, helping make the device comfortable for use by a wide variety of users' faces.

The bridge portion 110 of the example device 500 includes a series of slots 504 on its sides that can help avoid condensation building up on the inner surface of the device.

I claim:

1. A wearable protective device (100) including:
    a holder (106) for a removable breathing filter (400), the holder (106) including a bridge portion (110) configured, in use, to fit on a nose bridge of a wearer;
    an eye shield (102) connected to the bridge portion (110) of the holder (106) by means of at least one fixing device (122, 136, 128) that extends through at least one corresponding aperture in the holder and the eye shield; and
    an arrangement (104, 118) for fixing the device, in use, to a wearer's head, wherein the eye shield and the holder are integrated or permanently connected together.

2. A device according to claim 1, wherein the eye shield (102) and the holder (106) are integrated or permanently connected together so that they cannot be separated in a non-destructive manner.

3. A device according to claim 1, wherein the lenses are designed to provide eye protection only and not to correct eyesight defects.

4. A device according to claim 1, wherein the holder (106) is pivotable with respect to the eye shield (102).

5. A device according to claim 4, wherein the holder (106) is semi-rigid and is configured, in use, to receive/fit around at least part of an outer edge of a removable breathing filter (400).

6. A device according to claim 1, wherein the fixing device includes a moulded plastic pin (122).

7. A device according to claim 1, wherein a first portion of a flexible member (502) is fixed to the eye shield (102) and a second portion of the flexible member is fixed to the holder (106).

8. A device according to claim 7, wherein the first portion of the flexible member (502) is fixed to a substantially central portion of the eye shield (102) and the second portion of the flexible member is fixed to a substantially central portion of the bridge portion (110) of the holder (106).

9. A device according to claim 1, wherein the bridge portion (110) includes at least one slot (504) or aperture adapted to assist with avoiding condensation developing within the holder (106).

10. A device according to claim 1, wherein the fixing arrangement includes at least one elastic strap (118A, 118B) connected to at least one corresponding side portion/edge of the holder (106).

11. A device according to claim 10, including at least two said elastic straps (118A, 118B), each of the elastic straps including an interengageable clasp (120A, 120B) or clip at its free end.

12. A device according to claim 11, wherein the at least one elastic strap (118) is, in use, generally aligned with a mouth region of a wearer.

13. A device according to claim 4, wherein the removable breathing filter (400) is configured to be worn over a nose and mouth of the wearer and the removable breathing filter is disposable.

14. A wearable protective device (100) including:
a holder (106) for a removable breathing filter (400), the holder (106) including a bridge portion (110) configured, in use, to fit on a nose bridge of a wearer;
an eye shield (102) connected to the bridge portion (110) of the holder (106) by means of at least one fixing device (122, 136, 128) that extends through at least one corresponding aperture in the holder and the eye shield; and
an arrangement (104, 118) for fixing the device, in use, to a wearer's head, wherein the holder is pivotable with respect to the eye shield.

* * * * *